(12) United States Patent
Sakatani et al.

(10) Patent No.: US 10,632,139 B2
(45) Date of Patent: *Apr. 28, 2020

(54) OPHTHALMIC SOLUTION COMPRISING DIQUAFOSOL

(71) Applicant: Santen Pharmaceutical Co., Ltd., Osaka-shi, Osaka (JP)

(72) Inventors: Akiko Sakatani, Ikoma (JP); Tatsuo Ikei, Ikoma (JP); Koji Inagaki, Ikoma (JP); Masatsugu Nakamura, Ikoma (JP); Kazuhiro Hosoi, Ikoma (JP); Mikiko Saito, Ikoma (JP); Masaki Sonoda, Osaka (JP); Yoko Fukui, Osaka (JP); Mitsuaki Kuwano, Osaka (JP)

(73) Assignee: SANTEN PHARMACEUTICAL CO., LTD., Osaka-Shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/103,328

(22) Filed: Aug. 14, 2018

(65) Prior Publication Data

US 2018/0353531 A1 Dec. 13, 2018

Related U.S. Application Data

(63) Continuation of application No. 15/289,273, filed on Oct. 10, 2016, now Pat. No. 10,071,113, which is a continuation of application No. 14/386,169, filed as application No. PCT/JP2013/058519 on Mar. 25, 2013, now Pat. No. 9,486,529.

(30) Foreign Application Priority Data

Mar. 26, 2012 (JP) ................................ 2012-069157

(51) Int. Cl.
| | |
|---|---|
| A61K 31/7084 | (2006.01) |
| A61K 47/12 | (2006.01) |
| A61K 47/18 | (2017.01) |
| A61K 47/24 | (2006.01) |
| A61K 9/00 | (2006.01) |

(52) U.S. Cl.
CPC ........ *A61K 31/7084* (2013.01); *A61K 9/0048* (2013.01); *A61K 47/12* (2013.01); *A61K 47/183* (2013.01); *A61K 47/24* (2013.01)

(58) Field of Classification Search
CPC .. A61K 31/7084; A61K 47/183; A61K 47/12; A61K 9/0048; A61K 47/24
USPC .......................................................... 514/51
See application file for complete search history.

(56) References Cited

U.S. PATENT DOCUMENTS

| 5,504,113 A | 4/1996 | Lucero |
|---|---|---|
| 5,663,170 A | 9/1997 | Ushio et al. |
| 5,900,407 A | 5/1999 | Yerxa et al. |
| 6,333,045 B1 | 12/2001 | Yasueda et al. |
| 6,348,589 B1 | 2/2002 | Pendergast et al. |
| 6,583,181 B1 | 6/2003 | Chiang et al. |
| 6,984,629 B2 | 1/2006 | Nakata et al. |
| 9,486,529 B2 | 11/2016 | Sakatani et al. |
| 10,071,113 B2 * | 9/2018 | Sakatani ............ A61K 31/7084 |
| 2002/0103158 A1 | 8/2002 | Rideout et al. |
| 2003/0109488 A1 | 6/2003 | Yanni et al. |
| 2003/0186927 A1 | 10/2003 | Nakata et al. |
| 2010/0190734 A1 | 7/2010 | Brazzell et al. |
| 2010/0330164 A1 | 12/2010 | Yerxa et al. |
| 2012/0263803 A1 | 10/2012 | Mashima et al. |
| 2013/0172287 A1 | 7/2013 | Shichijo et al. |
| 2014/0221306 A1 | 8/2014 | Sakatani et al. |
| 2015/0072951 A1 | 3/2015 | Sakatani et al. |
| 2017/0020910 A1 | 1/2017 | Sakatani et al. |

FOREIGN PATENT DOCUMENTS

| AU | 2001260643 B2 | 6/2006 |
|---|---|---|
| CN | 1431914 A | 7/2003 |
| EP | 1428538 A1 | 6/2004 |

(Continued)

OTHER PUBLICATIONS

Petition, Invalidation Trial against counterpart Korean Patent No. 10-1875845, Case No. 2019 Dang 172 (Petitioner: Sam Chun Dang Pharmaceutical Co., Ltd.; Respondent: Santen Pharmaceutical Co., Ltd.), Filing Date: Jan. 15, 2019 (15 pages including partial English translation).

Package leaflet of DIQUAS® ophthalmic solution 3%: Exhibit B No. 1 of Reply Brief, Case No. 2018 Heo 7262, revised on Aug. 2012, (15 pages including partial English translation).

Petition, Invalidation Trial against counterpart Korean Patent No. 10-1935484, Case No. 2019 Dang 420 (Petitioner: Chong Kun Dang Pharmaceutical Co., Ltd.; Respondent: Santen Pharmaceutical Co., Ltd.), Filing Date: Jan. 31, 2019 (61 pages including partial English translation).

(Continued)

*Primary Examiner* — Yih-Horng Shiao
(74) *Attorney, Agent, or Firm* — Buchanan, Ingersoll & Rooney PC

(57) ABSTRACT

Regarding Diquafosol ophthalmic solution comprising a chelating agent at a concentration of 0.0001 to 1% (w/v), formation of insoluble precipitates found in Diquafosol ophthalmic solution during storage of the solution, as well as deterioration of the filtration performance in the course of production (course of filtration sterilization), have been inhibited. Further, in Diquafosol ophthalmic solution comprising a chelating agent, reduction of eye irritation and enhancement of the preservative effectiveness have been confirmed, in comparison to Diquafosol ophthalmic solution comprising no chelating agent. Accordingly, the present invention has been confirmed to provide physicochemical properties that are stable during the courses of production and distribution as well as the course of storage by a patient, and also reduce eye irritation and enhance preservative effectiveness.

10 Claims, 1 Drawing Sheet

(56) References Cited

FOREIGN PATENT DOCUMENTS

| | | |
|---|---|---|
| EP | 2614838 A1 | 7/2013 |
| EP | 2659894 A1 | 11/2013 |
| EP | 201390985 A1 | 11/2013 |
| EP | 2830634 A1 | 2/2015 |
| JP | H02164829 A | 6/1990 |
| JP | H05213757 A | 8/1993 |
| JP | 2001504858 A | 4/2001 |
| JP | 2001139493 A | 5/2001 |
| JP | 2002053492 A | 2/2002 |
| JP | 2003160491 A | 6/2003 |
| JP | 2005503325 A | 2/2005 |
| JP | 3652707 B2 | 3/2005 |
| JP | 2005330271 A | 12/2005 |
| JP | 2007182438 A | 7/2007 |
| JP | 2008247828 A | 10/2008 |
| JP | 2009040727 A | 2/2009 |
| JP | 2012149057 A | 8/2012 |
| JP | 2013227291 A | 11/2013 |
| JP | 5625081 B2 | 11/2014 |
| JP | 6126041 B2 | 5/2017 |
| KR | 1990074047 A | 10/1999 |
| KR | 20000070848 A | 11/2000 |
| KR | 20010031240 A | 4/2001 |
| KR | 100378443 B1 | 3/2003 |
| KR | 20030022740 A | 3/2003 |
| KR | 20030031489 A | 4/2003 |
| KR | 20060014375 A | 2/2006 |
| KR | 20070067189 A | 6/2007 |
| KR | 100832821 B1 | 5/2008 |
| KR | 20100121474 A | 11/2010 |
| KR | 10-2011-0104367 A1 | 9/2011 |
| KR | 10-1536885 B1 | 7/2015 |
| MX | 2013007502 A | 8/2013 |
| WO | 9834593 A1 | 8/1998 |
| WO | 0191795 A1 | 12/2001 |
| WO | 02060454 A2 | 8/2002 |
| WO | 2004091666 A1 | 10/2004 |
| WO | 2006059344 A1 | 6/2006 |
| WO | 2009097028 A1 | 8/2009 |
| WO | 2012/033189 A1 | 3/2012 |
| WO | 2012090994 A1 | 7/2012 |

OTHER PUBLICATIONS

Reply Brief, Invalidation Trial against counterpart Korean Patent, Case No. 2018 Heo 7262, (Petitioner: Santen Pharmaceutical Co., Ltd.; Respondent: Sam Chun Dang Pharmaceutical Co., Ltd.), Filing Date: Jan. 17, 2019 (32 pages including partial English translation).

Reply Brief, Invalidation Trial against counterpart Korean Patent, Case No. 2018 Heo 7286, (Petitioner: Santen Pharmaceutical Co., Ltd.; Respondent: Chong Kun Dang Pharmaceutical Co., Ltd.), Filing Date: Jan. 22, 2019 (74 pages including partial English translation).

Reply Brief, Invalidation Trial against counterpart Korean Patent, Case No. 2018 Heo 7293, (Petitioner: Santen Pharmaceutical Co., Ltd.; Respondent: Kukje Pharmaceutical Co., Ltd.), Filing Date: Feb. 18, 2019 (47 pages including partial English translation).

Petition for Correction: Exhibit B No. 1 of Reply Brief, Case No. 2018 Heo 7293, submitted on Sep. 12, 2017 (50 pages).

Manufacturing Pharmacy textbook, Mar. 1995: Exhibit A No. 6 of Petition, Invalidation Trial against counterpart Korean Patent No. 10-1875845, Case No. 2019 Dang 172 (10 pages including partial English translation).

Preparatory Brief in the Suit against Trial Decision for counterpart Korean Patent No. 1536885, Case No. 2018 Heo 6795 Invalidation Trial (Patent), Nov. 12, 2018 (39 pages including partial English translation).

International Search Report (PCT/ISA/210) dated May 7, 2013, by the Japanese Patent Office as the International Searching Authority for International Application No. PCT/JP2013/058519.

Tauber et al., "Double-Masked, Placebo-Controlled Safety and Efficacy Trail of Diquafosol Tetrasodium (INS365) Ophthalmic Solution for the Treatment of Dry Eye", Cornea, vol. 23, No. 8, Nov. 2004, pp. 784-792.

"Package Insert of DIQUAS® Ophthalmic Solution 3%", dated Apr. 2010, with Partial English Translation.

"Edetic Acid in Handbook of Pharmaceutical Excipients", with Partial English Translation, Feb. 8, 2007.

Final Decision for Rejection, dated Jan. 14, 2014, with English Translation.

Office Action issued by the U.S. Patent and Trademark Office in the U.S. Appl. No. 13/976,408, dated Oct. 7, 2014, U.S. Patent and Trademark Office, Alexandria, VA. (10 pages).

Search Report dated Aug. 8, 2014, by the Danish Patent and Trademark Office in corresponding Singapore Patent Application No. 2013050000 (3 pages).

Nichols et al.; "Diquafosol tetrasodium: a novel dry eye therapy", Expert Opinion on Investigational Drugs (2004), vol. 13, No, 1, pp. 47-54 (8 pages).

Anonymous: "Diquafosol, DE 089, Diquafosol Tetrasodium, INS 365, INS 365 Ophthalmic, INS 365 Respiratory, KPY 998", Drugs R&D (2003), vol. 4, No. 6, pp. 359-362 (4 pages).

First Office Action dated Jul. 1, 2014, by the State Intellectual Property Office of the People's Republic of China in Chinese Patent Application No. 201180063269.9, and an English translation of the Office Action. (10 pages).

International Search Report dated Jan. 31, 2012, by the European Patent Office in corresponding International Patent Application No. PCT/JP2011/080179, and an English translation (5 pages).

"As to Stability Guidelines", Apr. 21, 1994, New Drug No. 30, Partial English Translation (7 pages).

"Handbook for Proper Use of Ophthalmic Solution", Sep. 2011, Partial English Translation (25 pages).

"Pharmaceutical Products Interview Form" , Nov. 2010, Partial English Translation (47 pages).

Mundasad et al.; "Ocular Safety of INS365 Ophthalmic Solution: A $P2Y_2$ Agonist in Healthy Subjects", Journal of Ocular Pharmacology and Therapeutics (2001), vol. 17, No. 2, pp. 173-179 (7 pages).

The extended European Search Report dated Oct. 11, 2014, by the European Patent Office in corresponding European Patent Application No. 11852288.7-1460. (9 pages).

Office Action (Patent Examination Report No. 1) dated Feb. 23, 2015, by the Australian Patent Office in corresponding Australian Patent Application No. 2013241507 (3 pages).

Office Action issued by the New Zealand Patent Office in corresponding New Zealand Patent Application No. 631041 dated Jun. 23, 2015 (3 pages).

Office Action issued by the Georgian Patent Office in corresponding Georgian Patent Application No. AP 2013 013609 dated Aug. 3, 2015 (15 pages).

Office Action issued by the European Patent Office in corresponding European Patent Application No. 13770386.4 dated Oct. 19, 2015 (3 pages).

Office Action issued by the European Patent Office in corresponding Eurasian Patent Application No. 201491771 dated Oct. 22, 2015 (2 pages).

Search Report and Written Opinion issued by the Intellectual Property Office of Singapore in corresponding Singapore Patent Application No. 10201508591U dated Mar. 7, 2017 (4 pages).

Decision to Grant a Patent issued by the Japanese Patent Office in corresponding Japanese Patent Application No. 2014-082821 dated Mar. 7, 2017 (6 pages including partial English translation).

Office Action issued by the Mexican Patent Office in counterpart National Phase PCT Mexican Patent Application No. MX/a/2014/011468 dated Jun. 29, 2017 (6 pages including partial English translation).

Invalidation Trial against counterpart Korean Patent No. 1536885, Case No. 2017 Dang 1569, Petitioned by Sam Chun Dang Pharm. Co., Ltd., with Santen Pharmaceutical Co., Ltd. being the Respondent, mailed Jun. 9, 2017 by the Korean Patent Office (17 pages including partial English translation).

Invalidation Trial against counterpart Korean Patent No. 1536885, Case No. 2017 Dang 1658, Petitioned by Hanmi Pharm. Co., Ltd.,

(56) References Cited

OTHER PUBLICATIONS with Santen Pharmaceutical Co., Ltd. being the Respondent, mailed Jun. 19, 2017 by the Korean Patent Office (73 pages including partial English translation).
Japanese PMDA Examination Report for Diquas, Evaluation and Licensing Division, Pharmaceutical and Food Safety Bureau, Ministry of Health, Labour and Welfare, Mar. 5, 2010 (49 pages including partial English translation).
Handbook of Pharmaceutical Excipients, (Sixth Edition), 2009, (13 pages including partial English translation).
Invalidation Trial against counterpart Korean Patent No. 1536885, Case No. 2017 Dang 1676, Petitioned by Kukje Pharma Co., Ltd., with Santen Pharmaceutical Co., Ltd. being the Respondent, mailed Jun. 19, 2017 by the Korean Patent Office (29 pages including partial English translation).
Invalidation Trial against counterpart Korean Patent No. 1536885, Case No. 2017 Dang 1677, Petitioned by SAMIL Pharmaceutical Co., Ltd., with Santen Pharmaceutical Co., Ltd. being the Respondent, mailed Jun. 14, 2017 by the Korean Patent Office (29 pages including partial English translation).
Invalidation Trial against counterpart Korean Patent No. 1536885, Case No. 2017 Dang 1678, Petitioned by INTRO Pharm & Tech, with Santen Pharmaceutical Co., Ltd. being the Respondent, mailed Jun. 19, 2017 by the Korean Patent Office (29 pages including partial English translation).
"Pharmaceutics", Korean Association of Colleges of Pharmacy, Department of Pharmaceutics, National Academy of Medicine of Korea, Hanrimwon Publishing Co., Ltd., pp. 161-172 and 401-417, Mar. 2, 1996, (32 pages including partial English translation).
Invalidation Trial against counterpart Korean Patent No. 1536885, Case No. 2017 Dang 1698, Petitioned by Chong Kun Dang Pharmaceutical Corp., with Santen Pharmaceutical Co., Ltd. being the Respondent, mailed Jun. 13, 2017 by the Korean Patent Office (37 pages including partial English translation).
Handbook of Pharmaceutical Excipients, (Third Edition), Published by the American Pharmaceutical Association, Washington, DC, 2000 (3 pages).
Invalidation Trial against counterpart Korean Patent No. 1536885, Case No. 2017 Dang 1569, Petitioned by Sam Chun Dang Pharm. Co., Ltd., with Santen Pharmaceutical Co., Ltd. being the Respondent, mailed Oct. 16, 2017 by the Korean Patent Office (20 pages including partial English translation).
Notice of Grounds of Rejection issued by the Japanese Patent Office in corresponding Japanese Patent Application No. 2017-075167 dated Dec. 19, 2017 (4 pages including partial English translation).
Petition, Invalidation Trial against counterpart Korean Patent No. 1536885, Case No. 2017 Dang 1676 (Petitioner: Kukje Pharmo Co., Ltd.; Respondent: Santen Pharmaceutical Co., Ltd.), dated Feb. 9, 2018, Korean Patent Office (34 pages including partial English translation).
Petition, Invalidation Trial against counterpart Korean Patent No. 1536885, Case No. 2017 Dang 1677 (Petitioner: SAMIL Pharmaceutical Co., Ltd.; Respondent: Santen Pharmaceutical Co., Ltd.), dated Feb. 9, 2018, Korean Patent Office (34 pages including partial English translation).
Petition, Invalidation Trial against counterpart Korean Patent No. 1536885, Case No. 2017 Dang 1678 (Petitioner: Intro Biopharma; Respondent: Santen Pharmaceutical Co., Ltd.), dated Feb. 8, 2018, Korean Patent Office (33 pages including partial English translation).
Ministry of Food and Drug Safety (MFDS), Guideline for evaluation of pharmacy additive, May, 2007, (93 pages including partial English translation).
Prior Art Search (for Advancement of Examination) issued by the Korean Patent Office in corresponding Korean Patent Application No. 10-2015-7004372 dated Feb. 23, 2018 (18 pages including partial English translation).
Wikipedia material for Ethylenediaminetetraacetic acid, Internet printout, last edited Jan. 10, 2018 (9 pages).

Decision for Grant of Patent issued by the Korean Intellectual Property Office in counterpart Korean Patent Application No. 10-2015-7004372 dated Jun. 7, 2018 (4 pages including partial English translation).
Petition, Invalidation Trial against counterpart Korean Patent No. 1536885, Trial No. 2017 Dang 1698 (Plaintiff: Chong Kun Dang Pharmaceutical Corp.; Defendant: Santen Pharmaceutical Co., Ltd. ), Issuance No. 7-7-2018-002499267; Issuance Date: Apr. 11, 2018, The Korean Intellectual Property Tribunal, The 7th Bureau, (86 pages including partial English translation).
Korean Intellectual Property Office: "Patent and Utility Model Examination Guidelines," (a revision dated Nov. 21, 2016, established rule No. 94 of the Patent Office) pp. 3222, 3223, 3304, 3307, 3309, 3410 and 3411, (12 pages including partial English translation).
"Manufacturing Pharmaceutics," Book (Pharmacy, a revised edition in 2000), pp. 443, (4 pages including partial English translation).
Internet Printout: "List of Patented Pharmaceuticals," Ministry of Food and Drug Safety, (Patent list for registration of a pharmaceutical product related to the subject patented invention) Feb. 6, 2017, (2 pages including partial English translation).
Internet Printout: "Product Detailed View of Pharmaceuticals," Ministry of Food and Drug Safety, (detailed product information of Ministry of Food and Drug Safety on Diquas-S ophthalmic solution) Nov. 10, 2016, (5 pages including partial English translation).
"General Rules of Formulations," 9th revision on the general rules of formulations, the Korean Pharmacopeia, 2007, (6 pages including partial English translation).
"Interview Form on Pharmaceuticals," Japanese Standard Product Classification No. 871319, interview form on a Japanese hyaluronic acid ophthalmic solution, Eyecare®, Feb. 2011, (34 pages including partial English translation).
Freeman et al.: "Preservatives in Topical Ophthalmic Medications: Historical and Clinical Perspectives," (Thesis, Expert Rev Ophthalmol, 2009; 4(1): 59-64)(6 pages).
3rd Appeal Brief filed by Sam Chun Dang Pharm Co., Ltd.; Invalidation Trial against counterpart Korean Patent No. 1536885, Trial No. 2017 Dang 1569 against Santen Pharmaceutical Co., Ltd. on Jun. 14, 2018 (19 pages including partial English translation).
Exhibit A No. 7 "Pharmaceutics" from 3rd Appeal Brief filed by Sam Chun Dang Pharm Co., Ltd.; Invalidation Trial against counterpart Korean Patent No. 1536885, Trial No. 2017 Dang 1569 against Santen Pharmaceutical Co., Ltd., on Jun. 14, 2018 (6 pages including partial English translation).
Board of Trials 7th Division Decision; Invalidation Trial against counterpart Korean Patent No. 1536885, Trial No. 2017 Dang 1569 against Santen Pharmaceutical Co., Ltd., issued on Jun. 29, 2018 (54 pages including partial English translation).
2nd Appeal Brief filed by Hanmi Pharm. Co., Ltd.; Invalidation Trial against counterpart Korean Patent No. 1536885, Trial No. 2017 Dang 1658 against Santen Pharmaceutical Co., Ltd. on Jun. 11, 2018 (76 pages including partial English translation).
Reference Material 1 from 2nd Appeal Brief filed by Hanmi Pharm. Co., Ltd.; Invalidation Trial against counterpart Korean Patent No. 1536885, Trial No. 2017 Dang 1658 against Santen Pharmaceutical Co., Ltd. on Jun. 11, 2018, entitled, "General Test Method," Korean Pharmacopoeia, 9th Revised Edition (KP IX) (24 pages including partial English translation).
3rd Appeal Brief filed by Hanmi Pharm. Co., Ltd.; Invalidation Trial against counterpart Korean Patent No. 1536885, Trial No. 2017 Dang 1658 against Santen Pharmaceutical Co., Ltd. on Jun. 18, 2018 (24 pages including partial English translation).
Board of Trials 7th Division Decision; Invalidation Trial against counterpart Korean Patent No. 1536885, Trial No. 2017 Dang 1658 against Santen Pharmaceutical Co., Ltd., issued on Jun. 29, 2018 (55 pages including partial English translation).
3rd Appeal Brief filed by Kukje; Invalidation Trial against counterpart Korean Patent No. 1536885, Trial No. 2017 Dang 1676 against Santen Pharmaceutical Co., Ltd. on Jun. 19, 2018 (24 pages including partial English translation).
3rd Appeal Brief filed by Samil; Invalidation Trial against counterpart Korean Patent No. 1536885, Trial No. 2017 Dang 1677 against

(56) References Cited

OTHER PUBLICATIONS

Santen Pharmaceutical Co., Ltd. on Jun. 19, 2018 (24 pages including partial English translation).
3rd Appeal Brief filed by Introbio Pharma; Invalidation Trial against counterpart Korean Patent No. 1536885, Trial No. 2017 Dang 1678 against Santen Pharmaceutical Co., Ltd. on Jun. 19, 2018 (24 pages including partial English translation).
Board of Trials 7th Division Decision; Invalidation Trial against counterpart Korean Patent No. 1536885, Trial No. 2017 Dang 1676, 2017 Dang 1677, and 2017 Dang 1678 against Santen Pharmaceutical Co., Ltd., issued on Jun. 29, 2018 (54 pages including partial English translation).
3rd Appeal Brief filed by Chong Kun Dang Co., Ltd.; Invalidation Trial against counterpart Korean Patent No. 1536885, Trial No. 2017 Dang 1698 against Santen Pharmaceutical Co., Ltd. on Jun. 18, 2018 (35 pages including partial English translation).
Reference Material 9 from 3rd Appeal Brief filed by Chong Kun Dang Co., Ltd.; Invalidation Trial against counterpart Korean Patent No. 1536885, Trial No. 2017 Dang 1698 against Santen Pharmaceutical Co., Ltd. on Jun. 18, 2018, Patent Court Decision 2008 Heo 6062, (6 pages).
Reference Material 10 from 3rd Appeal Brief filed by Chong Kun Dang Co., Ltd.; Invalidation Trial against counterpart Korean Patent No. 1536885, Trial No. 2017 Dang 1698 against Santen Pharmaceutical Co., Ltd. on Jun. 18, 2018, Supreme Court Decision 96 Hu 1514, (2 pages).
Reference Material 11 from 3rd Appeal Brief filed by Chong Kun Dang Co., Ltd.; Invalidation Trial against counterpart Korean Patent No. 1536885, Trial No. 2017 Dang 1698 against Santen Pharmaceutical Co., Ltd. on Jun. 18, 2018, Supreme Court Decision 2004 Hu 2307, (2 pages).
Reference Material 12 from 3rd Appeal Brief filed by Chong Kun Dang Co., Ltd.; Invalidation Trial against counterpart Korean Patent No. 1536885, Trial No. 2017 Dang 1698 against Santen Pharmaceutical Co., Ltd. on Jun. 18, 2018, General Chemistry by Steven S. Zumdahl, Ilshin Publishing Company, (5 pages).
Reference Material 13 from 3rd Appeal Brief filed by Chong Kun Dang Co., Ltd.; Invalidation Trial against counterpart Korean Patent No. 1536885, Trial No. 2017 Dang 1698 against Santen Pharmaceutical Co., Ltd. on Jun. 18, 2018, entitled, "PHARMACEUTICS," Hanrimwon Publishing Company, (7 pages including partial English translation).
4th Appeal Brief filed by Chong Kun Dang Co., Ltd.; Invalidation Trial against counterpart Korean Patent No. 1536885, Trial No. 2017 Dang 1698 against Santen Pharmaceutical Co., Ltd. on Jun. 27, 2018 (23 pages including partial English translation).
Reference Material 14 from 4th Appeal Brief filed by Chong Kun Dang Co., Ltd.; Invalidation Trial against counterpart Korean Patent No. 1536885, Trial No. 2017 Dang 1698 against Santen Pharmaceutical Co., Ltd. on Jun. 27, 2018, entitled, "PHARMACOLOGY," Hanrimwon Publishing Company, Korean Parmacopoeia, (5 pages including partial English translation).
Reference Material 15 from 4th Appeal Brief filed by Chong Kun Dang Co., Ltd.; Invalidation Trial against counterpart Korean Patent No. 1536885, Trial No. 2017 Dang 1698 against Santen Pharmaceutical Co., Ltd. on Jun. 27, 2018, Patent and Utility Model Guidelines for Examination, (4 pages).
Board of Trials 7th Division Decision; Invalidation Trial against counterpart Korean Patent No. 1536885, Trial No. 2017 Dang 1698 against Santen Pharmaceutical Co., Ltd., issued on Jun. 29, 2018 (58 pages including partial English translation).
"Preparatory Brief in the Suit against Trial Decision (2018 Heo 7293)", Jun. 3, 2019.
Exhibit: Handbook of Pharmaceutical Excipients, edited by Ainley Wade et al., Second Edition, 1994, pp. 176-179.
"Preparatory Brief in the Suit against Trial Decision (2018 Heo 7262)", Jun. 7, 2019.
"Preparatory Brief in the Suit against Trial Decision (2018 Heo 7286)", Jun. 10, 2019.
Rebuttal Brief, Invalidation Trial against counterpart Korean Patent No. 1875845, Case No. 2019 Dang 172 (Petitioner: Sam Chun Dang Pharmaceutical Co., Ltd.; Respondent: Santen Pharmaceutical Co., Ltd.), Filing Date: Jul. 31, 2019 (26 pages including partial English translation).
The Korean Pharmacopoeia, Commentary of 7th revision, Compiled by Korean Association of College of Pharmacy Pharmacopoeia Division, 2001: Exhibit A No. 9 of Rebuttal Brief, Invalidation Trial against counterpart Korean Patent No. 1875845, Case No. 2019 Dang 172 (6 pages including partial English translation).
Pharmaceutical Dosage Forms: A Series of Pharmaceutics (1), Published by Division of Pharmaceutics, Mar. 2, 2000: Exhibit A No. 10 of Rebuttal Brief, Invalidation Trial against counterpart Korean Patent No. 1875845, Case No. 2019 Dang 172 (4 pages including partial English translation).
Preparatory Brief, Invalidation Trial against counterpart Korean Patent, Case No. 2018 Heo 6795, (Petitioner: Hanmi Pharmaceutical Co., Ltd.; Respondent: Santen Pharmaceutical Co., Ltd.), Filing Date: Aug. 13, 2019 (7 pages including partial English translation).
Supplemental Brief, Invalidation Trial against counterpart Korean Patent, Case No. 2018 Heo 7286, (Petitioner: Santen Pharmaceutical Co., Ltd.; Respondent: Chong Kun Dang Pharmaceutical Co., Ltd.), Filing Date: Aug. 19, 2019 (18 pages including partial English translation).
Decision in Invalidation Trial against counterpart Korean Patent, Case No. 2018 Heo 6795, (Plaintiff: Hanmi Pharmaceutical Co., Ltd.; Defendant: Santen Pharmaceutical Co., Ltd.), Mailing Date: Sep. 16, 2019 (39 pages including partial English translation).
Decision in Invalidation Trial against counterpart Korean Patent, Case No. 2018 Heo 7262, (Plaintiff: Santen Pharmaceutical Co., Ltd.; Defendant: Sam Chun Dang Pharmaceutical Co., Ltd.), Mailing Date: Sep. 16, 2019 (45 pages including partial English translation).
Decision in Invalidation Trial against counterpart Korean Patent, Case No. 2018 Heo 7279, (Plaintiff: Santen Pharmaceutical Co., Ltd.; Defendant: Hanmi Pharmaceutical Co., Ltd.), Mailing Date: Sep. 16, 2019 (42 pages including partial English translation).
Decision in Invalidation Trial against counterpart Korean Patent, Case No. 2018 Heo 7286, (Plaintiff: Santen Pharmaceutical Co., Ltd.; Defendant: Chong Kun Dang Pharmaceutical Co., Ltd.), Mailing Date: Sep. 16, 2019 (44 pages including partial English translation).
Decision in Invalidation Trial against counterpart Korean Patent, Case No. 2018 Heo 7293, (Plaintiff: Santen Pharma Co., Ltd.; Defendant: Kukje Pharmaceutical Co., Ltd.), Mailing Date: Sep. 16, 2019 (42 pages including partial English translation).
Exhibit A, No. 24 of Rebuttal Brief in the Invalidation Trial against counterpart Korean Patent, Case No. 2019 Dang 420, Printout of Korean Supreme Court's homepage, Case No. 2018 Heo 7286, (Plaintiff: Santen Pharmaceutical Co., Ltd.; Defendant: Chong Kun Dang Pharmaceutical Corp.), Printed on Oct. 14, 2019 (3 pages including partial English translation).
Exhibit A, No. 25, "Pharmaceutical Dosage Forms" of Rebuttal Brief in the Invalidation Trial against counterpart Korean Patent, Case No. 2019 Dang 420, 1995, pp. 21-31 (19 pages including partial English translation).
Exhibit A, No. 26, "Pharmaceutical Dosage Forms" of Rebuttal Brief in the Invalidation Trial against counterpart Korean Patent, Case No. 2019 Dang 420, 1995, pp. 439-443 (10 pages including partial English translation).
Rebuttal Brief in the Invalidation Trial against counterpart Korean Patent, Case No. 2019 Dang 420, (Petitioner: Chong Kun Dang Pharmaceutical Co., Ltd.; Respondent: Santen Pharmaceutical Co., Ltd.), Filing Date: Oct. 16, 2019 (41 pages including partial English translation).
Office Action issued by the Korean Patent Office in corresponding Korean Patent Application No. 10-2018-7037979 dated Dec. 2, 2019 (9 pages including partial English translation).
Rebuttal Brief in the lnvalidation Trial against counterpart Korean Patent No. 1875845, Case No. 2019 Dang 172, (Petitioner: Sam

(56) References Cited

OTHER PUBLICATIONS

Chun Dang Pharmaceutical Co., Ltd.; Respondent: Santen Pharmaceutical Co., Ltd.), Filing Date: Dec. 10, 2019 (23 pages including partial English translation).

Reference No. 2 of Rebuttal Brief in the Invalidation Trial against counterpart Korean Patent. No. 1875845, Case No. 2019 Dang 172: Supreme Court Decision, Supreme Court Case No. 2003 Hu 2010, dated Apr. 15, 2005 (4 pages including partial English translation).

Reference No. 3 of Rebuttal Brief in the Invalidation Trial against counterpart Korean Patent No. 1875845, Case No. 2019 Dang 172: Patent Court Decision, Case No. 2018 Heo 7262 Invalidation (Patent), dated Sep. 6, 2019 (45 pages including partial English translation).

Decision in the Invalidation Trial against counterpart Korean Patent No. 1536885, Trial Case No. 2019 Dang (Revocation Decision) 138, (Petitioner: Hanmi Pharmaceutical Co., Ltd.; Respondent: Santen Pharmaceutical Co., Ltd.), issued by the Trial Board, Division No. 7, on Feb. 11, 2020 (19 pages including partial English translation).

\* cited by examiner

□ FORMULATION CONTAINING POLYPHOSPHATE
▲ FORMULATION CONTAINING CITRIC ACID
△ FORMULATION CONTAINING METAPHOSPHATE
● FORMULATION CONTAINING EDETATE
○ FORMULATION CONTAINING NO CHELATING AGENT

OPHTHALMIC SOLUTION COMPRISING DIQUAFOSOL

CROSS-REFERENCE TO RELATED APPLICATIONS

This application is a continuation of U.S. application Ser. No. 15/289,273, filed Oct. 10, 2016, which is a continuation of U.S. application Ser. No. 14/386,169, filed Sep. 18, 2014, which is now U.S. Pat. No. 9,486,529, which is a U.S. National Stage Application of PCT/JP2013/058519, filed Mar. 25, 2013, which claims priority to Japanese Patent Application No. 2012-069157, filed Mar. 26, 2012, the contents of all of which are hereby incorporated by reference.

TECHNICAL FIELD

The present invention relates to an aqueous ophthalmic solution comprising diquafosol or a salt thereof at a concentration of 0.1 to 10% (w/v) and a chelating agent at a concentration of 0.0001 to 1% (w/v), and relates to a method for producing this ophthalmic solution. The present invention also relates to a method for inhibiting formation of insoluble precipitates in an aqueous ophthalmic solution comprising diquafosol or a salt thereof at a concentration of 0.1 to 10% (w/v) (hereinafter also referred to simply as "Diquafosol ophthalmic solution"), by adding a chelating agent at a concentration of 0.0001 to 1% (w/v) to the aqueous ophthalmic solution, a method for reducing eye irritation caused by the aqueous ophthalmic solution, and a method for enhancing preservative effectiveness of the aqueous ophthalmic solution.

BACKGROUND ART

Diquafosol is a purinergic receptor agonist also called $P^1,P^4$-di(uridine-5')tetraphosphate or $Up_4U$, and is known to have an effect of stimulating secretion of tears as disclosed in Japanese Patent No. 3652707 (PTD 1). Cornea, 23(8), 784-792 (2004) (NPD 1) describes that instillation of an ophthalmic solution comprising diquafosol tetrasodium salt has improved corneal epithelium disorder of dry eye patients. In our country, an ophthalmic solution comprising diquafosol tetrasodium salt at a concentration of 3% (w/v) is actually used as a remedy for dry eyes (product name: DIQUAS (registered trademark) ophthalmic solution 3%).

As for an ophthalmic solution, it is necessary for the solution to have physicochemical properties that are stable during the courses of production and distribution as well as the course of storage by a patient. In particular, regarding such an ophthalmic solution as the one in which precipitates are formed during the course of distribution or during storage by a patient, the precipitates cannot be removed afterward, and therefore such an ophthalmic solution is undesirable for use as an ophthalmic solution. Although precipitates formed in an ophthalmic solution during the course of its production can be removed in the process of filtration sterilization of the ophthalmic solution, a filter is clogged during the filtration to accordingly deteriorate the efficiency of filtration sterilization, resulting in a problem of an increase of the production cost.

As to a method for inhibiting formation of precipitates in an ophthalmic solution, Japanese Patent Laying-Open No. 2007-182438 (PTD 2) discloses a method according to which glycerin is added to the ophthalmic solution, for example. As described in this document, the properties and/or the state of precipitates vary depending on the type of active ingredient and/or the type of additive, and accordingly the method for inhibiting formation of precipitates varies depending on the ophthalmic solution.

CITATION LIST

Patent Document

PTD 1: Japanese Patent No. 3652707
PTD 2: Japanese Patent Laying-Open No. 2007-182438

Non Patent Document

NPD 1: Cornea, 23(8), 784-792 (2004)

SUMMARY OF INVENTION

Technical Problem

Thus, it is a challenge of interest to seek Diquafosol ophthalmic solution having stable physicochemical properties and a method for producing the same.

Solution to Problem

The inventors of the present invention have carried out thorough studies to consequently find that insoluble precipitates are formed over time in Diquafosol ophthalmic solution during storage of the solution, and that addition of a chelating agent at a concentration of 0.0001 to 1% (w/v) can inhibit formation of the insoluble precipitates, and thereby reach the present invention. The inventors of the present invention have also found that addition of a chelating agent at a concentration of 0.0001 to 1% (w/v) to Diquafosol ophthalmic solution can reduce eye irritation caused by the ophthalmic solution and enhance the preservative effectiveness of the solution.

Specifically, the present invention provides an aqueous ophthalmic solution comprising diquafosol or a salt thereof at a concentration of 0.1 to 10% (w/v) and a chelating agent at a concentration of 0.0001 to 1% (w/v) (hereinafter referred to simply as "the present ophthalmic solution").

The chelating agent in the present ophthalmic solution is preferably at least one type selected from the group consisting of edetic acid, citric acid, metaphosphoric acid, pyrophosphoric acid, polyphosphoric acid, malic acid, tartaric acid, phytic acid, and salts thereof; more preferably at least one type selected from the group consisting of edetic acid, citric acid, metaphosphoric acid, polyphosphoric acid, and salts thereof; and particularly preferably a salt of edetic acid.

In the present ophthalmic solution, the chelating agent is preferably at a concentration of 0.0005 to 0.5% (w/v), and particularly preferably at 0.001 to 0.1% (w/v) in the ophthalmic solution.

In the present ophthalmic solution, diquafosol or a salt thereof is at a concentration of preferably 1 to 10% (w/v), and particularly preferably 3% (w/v) in the ophthalmic solution.

Regarding the present ophthalmic solution, it is preferable that the chelating agent is a salt of edetic acid, the chelating agent is at a concentration of 0.001 to 0.1% (w/v) in the ophthalmic solution, and diquafosol or a salt thereof is at a concentration of 3% (w/v) in the ophthalmic solution.

Preferably, the present ophthalmic solution further comprises a preservative.

The present invention also provides a method for producing an aqueous ophthalmic solution comprising diquafosol or a salt thereof at a concentration of 0.1 to 10% (w/v), comprising the step of mixing diquafosol or a salt thereof and a chelating agent in an amount that causes a final concentration of the chelating agent in the aqueous ophthalmic solution to be 0.0001 to 1% (w/v), to obtain an aqueous solution in which formation of insoluble precipitates is inhibited (hereinafter referred to simply as "the present method for production").

Preferably, the present method for production further comprises the step of filtering the obtained aqueous solution through a filtration sterilization filter having a pore size of 0.1 to 0.5 μm.

The present invention further provides a method for inhibiting formation of insoluble precipitates in an aqueous ophthalmic solution comprising diquafosol or a salt thereof at a concentration of 0.1 to 10% (w/v), by adding a chelating agent at a concentration of 0.0001 to 1% (w/v) to the aqueous ophthalmic solution.

The present invention further provides a method for reducing eye irritation caused by an aqueous ophthalmic solution comprising diquafosol or a salt thereof at a concentration of 0.1 to 10% (w/v), by adding a chelating agent at a concentration of 0.0001 to 1% (w/v) to the aqueous ophthalmic solution.

The present invention further provides a method for enhancing preservative effectiveness of an aqueous ophthalmic solution comprising diquafosol or a salt thereof at a concentration of 0.1 to 10% (w/v), by adding a chelating agent at a concentration of 0.0001 to 1% (w/v) to the aqueous ophthalmic solution.

Advantageous Effects of Invention

As is clear from the results of a storage stability test and a filtration performance test described later herein, according to the present ophthalmic solution, Diquafosol ophthalmic solution not comprising a chelating agent has been found to inhibit formation of insoluble precipitates during storage which are found in Diquafosol ophthalmic solution, as well as deterioration of filtration performance in the course of production (course of filtration sterilization). Further, as proved by the results of an eye irritation evaluation test and a preservative effectiveness test described later herein, the present ophthalmic solution has been confirmed as reducing eye irritation and having enhanced preservative effectiveness in comparison to Diquafosol ophthalmic solution comprising no chelating agent. Accordingly, the present ophthalmic solution has physicochemical properties that are stable during the courses of production and distribution as well as the course of storage by a patient. In addition, the present ophthalmic solution allows reduction of eye irritation and has excellent preservative effectiveness. In particular, since degradation of the filtration performance in the course of production (course of filtration sterilization) is inhibited, the present ophthalmic solution can be subjected to efficient filtration sterilization in the course of production, thereby contributing to a decrease in production cost.

DESCRIPTION OF EMBODIMENTS

Figure 1:
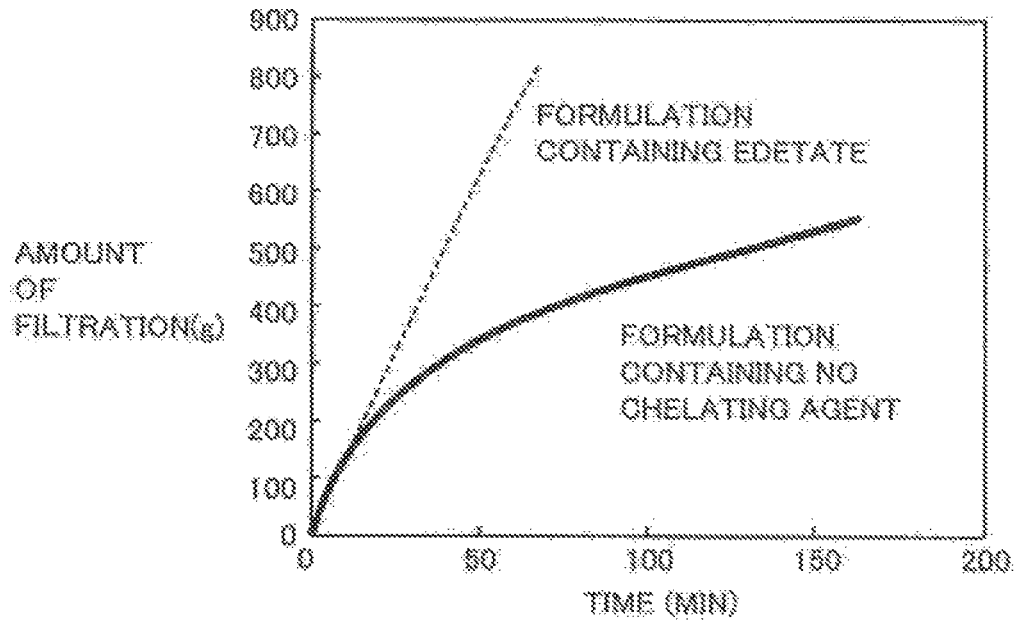
FIG. 1 is a graph showing the results of a filtration performance test conducted for each Diquafosol ophthalmic solution of a formulation containing edetate and a formulation containing no chelating agent, where the vertical axis represents the amount of filtration (g) and the horizontal axis represents the time (minutes).

Diquafosol is a compound represented by the following structural formula.

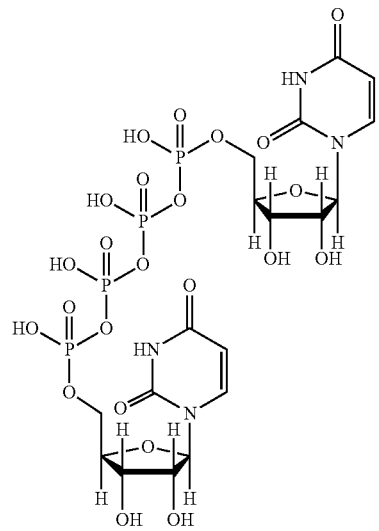

"A salt of diquafosol" is not particularly limited as long as it is a pharmaceutically acceptable salt, and may for example be: a metal salt with lithium, sodium, potassium, calcium, magnesium, zinc, or the like; a salt with an inorganic acid such as hydrochloric acid, hydrobromic acid, hydriodic acid, nitric acid, sulfuric acid, or phosphoric acid; a salt with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethane sulfonic acid, benzenesulfonic acid, p-toluene sulfonic acid, lauryl sulfate ester, methyl sulfate, naphthalene sulfonic acid, or sulfosalicylic acid; a quaternary ammonium salt with methyl bromide, methyl iodide, or the like; a salt with halogen ion such as bromine ion, chlorine ion, or iodine ion; a salt with ammonia; or a salt with organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, or N,N-bis(phenylmethyl)-1,2-ethanediamine.

Regarding the present invention, "diquafosol or a salt thereof" also includes a hydrate and an organic solvate of diquafosol (free form) or a salt thereof.

In the case where diquafosol or a salt thereof has a crystal polymorph and a group of crystal polymorphs (crystal polymorph system), these crystal polymorph and group of crystal polymorphs (crystal polymorph system) are also included in the scope of the present invention. A group of crystal polymorphs (crystal polymorph system) herein means individual crystal forms in respective stages where the crystal form changes depending on conditions and states in manufacture, crystallization, storage and the like of the crystals, as well as the entire course of change.

"Diquafosol or a salt thereof" of the present invention is preferably a sodium salt of diquafosol, and particularly preferably diquafosol tetrasodium salt (hereinafter also referred to simply as "diquafosol sodium") represented by the following structural formula.

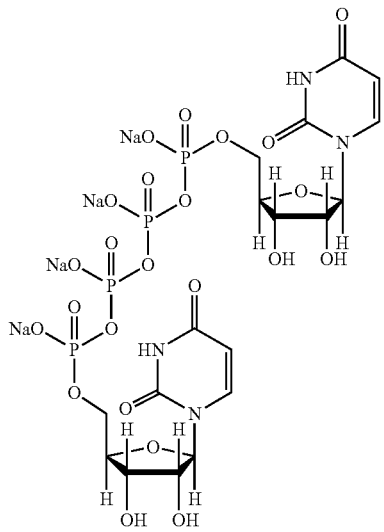

Diquafosol or a salt thereof can be produced in accordance with a method for example disclosed in Japanese National Patent Publication No. 2001-510484.

While the present ophthalmic solution may also comprise an active ingredient other than diquafosol or a salt thereof, the present ophthalmic solution preferably comprises diquafosol or a salt thereof as a sole active ingredient.

The concentration of diquafosol or a salt thereof in the present ophthalmic solution is 0.1 to 10% (w/v), which is preferably 1 to 10% (w/v) and particularly preferably 3% (w/v).

The present method for production uses diquafosol or a salt thereof in such an amount that causes the final concentration of diquafosol or a salt thereof in an aqueous ophthalmic solution obtained through this production method to be 0.1 to 10% (w/v), which is preferably an amount that causes the final concentration thereof to be 1 to 10% (w/v), and particularly preferably an amount that causes the final concentration thereof to be 3% (w/v).

Regarding the present invention, "aqueous ophthalmic solution" means an ophthalmic solution in which water is used as a solvent.

Regarding the present invention, "chelating agent" is not particularly limited as long as it is a compound that chelates metallic ions, and may for example be: edetic acid or a salt thereof such as edetic acid (ethylene diamine tetraacetic acid), monosodium edetate, disodium edetate, trisodium edetate, tetrasodium edetate, dipotassium edetate, tripotassium edetate, or tetrapotassium edetate; citric acid or a salt thereof such as citric acid, monosodium citrate, disodium citrate, trisodium citrate, monopotassium citrate, dipotassium citrate, or tripotassium citrate; metaphosphoric acid or a salt thereof such as metaphosphoric acid, sodium metaphosphate, or potassium metaphosphate; pyrophosphoric acid or a salt thereof such as pyrophosphoric acid, tetrasodium pyrophosphate, or tetrapotassium pyrophosphate; polyphosphoric acid or a salt thereof such as polyphosphoric acid, sodium polyphosphate, or potassium polyphosphate; malic acid or a salt thereof such as monosodium malate, disodium malate, monopotassium malate, or dipotassium malate; tartaric acid or a salt thereof such as sodium tartrate, potassium tartrate, or sodium potassium tartrate; or phytic acid or a salt thereof such as sodium phytate or potassium phytate. Regarding the present invention, "edetic acid, citric acid, metaphosphoric acid, pyrophosphoric acid, polyphosphoric acid, malic acid, tartaric acid, phytic acid, and salts thereof" also include hydrates and organic solvates of respective free forms or salts thereof.

Regarding the present invention, preferred chelating agents are edetic acid, a salt of edetic acid (edetate), citric acid, a salt of citric acid (citrate), metaphosphoric acid, a salt of metaphosphoric acid (metaphosphate), polyphosphoric acid, and a salt of polyphosphoric acid (polyphosphate), and particularly preferred chelating agents are a sodium salt of edetic acid (including hydrates such as disodium edetate hydrate), citric acid (including hydrates such as citric acid monohydrate), a sodium salt of metaphosphoric acid (sodium metaphosphate), and a sodium salt of polyphosphoric acid (sodium polyphosphate).

Regarding the present invention, a most preferred edetate is disodium edetate hydrate (hereinafter also referred to simply as "sodium edetate hydrate").

The concentration of the chelating agent in the present ophthalmic solution is 0.0001 to 1% (w/v), preferably 0.0005 to 0.5% (w/v), and particularly preferably 0.001 to 0.1% (w/v).

The amount of the chelating agent used by the present method for production is such an amount that causes the final concentration of the chelating agent in an aqueous ophthalmic solution obtained through this method to be 0.0001 to 1% (w/v), more preferably such an amount that causes the final concentration of the chelating agent to be 0.0005 to 0.5% (w/v), and particularly preferably such an amount that causes the final concentration of the chelating agent to be 0.001 to 0.1% (w/v).

The present ophthalmic solution may further comprise a preservative. "Preservative" of the present invention may for example be benzalkonium chloride, benzethonium chloride, chlorhexidine gluconate, paraben, sorbic acid, chlorobutanol, boric acid, or chlorite, and is particularly preferably benzalkonium chloride.

The most preferred benzalkonium chloride added to the present ophthalmic solution is a benzalkonium chloride represented by a general formula: $[C_6H_5CH_2N(CH_3)_2R]Cl$ where the carbon number of an alkyl group R is 12 (hereinafter also referred to simply as "BAK-$C_{12}$").

Regarding the present method for production, the aforementioned preservative may further be added when diquafosol or a salt thereof and a chelating agent are mixed together.

In the case where the present ophthalmic solution further comprises a preservative, the concentration of the preservative is not particularly limited as long as it exhibits predetermined preservative effectiveness. In the case where the preservative is benzalkonium chloride, the concentration thereof is preferably 0.0001 to 0.1% (w/v), more preferably 0.0005 to 0.01% (w/v), and particularly preferably 0.001 to 0.005% (w/v).

In the case where the present method for production further uses a preservative, the amount of the preservative to be used is not particularly limited as long as it exhibits predetermined preservative effectiveness. In the case where the preservative is benzalkonium chloride, the amount of the preservative is preferably such an amount that causes the final concentration of the preservative in an aqueous ophthalmic solution obtained through this method to be 0.0001 to 0.1% (w/v), more preferably such an amount that causes the final concentration thereof to be 0.0005 to 0.01% (w/v), and particularly preferably such an amount that causes the final concentration thereof to be 0.001 to 0.005% (w/v).

To the present ophthalmic solution, a generally-used art may be applied to add a pharmaceutically acceptable additive as required. For example, any of: buffer agents such as sodium phosphate, sodium hydrogen phosphate, sodium dihydrogen phosphate, sodium acetate, and epsilon aminocaproic acid; isotonizing agents such as sodium chloride, potassium chloride, and concentrated glycerin; surfactants such as polyoxyethylene sorbitan monooleate, polyoxyl 40 stearate, and polyoxyethylene hydrogenated castor oil, and the like may be selected as required and added to the present ophthalmic solution. The pH of the present ophthalmic solution may at least fall in an ophthalmologically acceptable range, and usually it preferably falls in a range of 4 to 8.

Regarding the present method for production, the aforementioned additive may further be added when diquafosol and a chelating agent are mixed together.

The present ophthalmic solution may be subjected to a filtration sterilization process or any of other sterilization processes, and the present ophthalmic solutions thus sterilized are also included in the scope of the present invention.

Regarding the present method for production, an aqueous solution obtained by mixing diquafosol or a salt thereof and a chelating agent together may further be sterilized. While the method for sterilization is not particularly limited as long as the method can sterilize the obtained aqueous solution, the method is preferably filtration sterilization.

Regarding the present invention, "filtration sterilization" is not particularly limited as long as it can sterilize the aqueous solution through filtering. Preferably, the solution is filtered through a filtration sterilization filter having a pore size of 0.1 to 0.5 μm.

Regarding the present invention, "insoluble precipitate" means a foreign body that has been formed in the course of production, distribution, and/or storage of the present ophthalmic solution and will not be dissolved again. "Formation of insoluble precipitate" regarding the present invention means both or one of: (a) a visible foreign body is formed in the ophthalmic solution; and (b) while no visible foreign body is formed in the ophthalmic solution, degradation of the filtration performance occurs during filtration sterilization.

Regarding the present invention, "formation of insoluble precipitates is inhibited" means that the ophthalmic solution comprising diquafosol or a salt thereof at a prescribed concentration shows both or one of: (a) reduction of the frequency of formation and/or the amount of visible foreign bodies in the ophthalmic solution that are found immediately after production or during storage of the ophthalmic solution (including the case where visible foreign bodies are not found at all); and (b) inhibition of deterioration of the filtration performance during filtration sterilization (including the case where deterioration of the filtration performance does not occur at all), in comparison to the ophthalmic solution comprising diquafosol or a salt thereof at the same concentration but comprising no chelating agent.

The present invention further provides a method for inhibiting formation of insoluble precipitates in an aqueous ophthalmic solution comprising diquafosol or a salt thereof, by adding a chelating agent at a concentration of 0.0001 to 1% (w/v) to the aqueous ophthalmic solution. Regarding the present invention, "inhibiting formation of insoluble precipitates" is used synonymously with "formation of insoluble precipitates is inhibited". The definition of each term regarding the method for inhibiting formation of insoluble precipitates is the same as described above, and preferred embodiments are similar to those as described above as well.

The present invention further provides a method for reducing eye irritation caused by an aqueous ophthalmic solution comprising diquafosol or a salt thereof, by adding a chelating agent at a concentration of 0.0001 to 1% (w/v) to the aqueous ophthalmic solution. Regarding the present invention, "reducing eye irritation" means that the occurrence frequency (occurrence rate) of eye irritation as a side effect caused when an ophthalmic solution comprising diquafosol or a salt thereof at a prescribed concentration is applied to a dry-eye patient is lower than that in the case of the ophthalmic solution comprising diquafosol or a salt thereof at the same concentration but not comprising a chelating agent. Furthermore, the definitions of other terms regarding the method for reducing eye irritation are the same as described above, and preferred embodiments are similar to those as described above as well.

The present invention further provides a method for enhancing preservative effectiveness of an aqueous ophthalmic solution comprising diquafosol or a salt thereof, by adding a chelating agent at a concentration of 0.0001 to 1% (w/v) to the aqueous ophthalmic solution. Regarding the present invention, "enhancing preservative effectiveness" means that the ophthalmic solution comprising diquafosol or a salt thereof at a prescribed concentration is less in the amount of a preservative that needs to be added for passing a preservative effectiveness test than the ophthalmic solution comprising diquafosol or a salt thereof at the same concentration but not comprising a chelating agent. Furthermore, the definitions of other terms regarding the method for enhancing preservative effectiveness are the same as described above, and preferred embodiments are similar to those as described above as well.

In the following, the results of a storage stability test, a filtration performance test, an eye irritation evaluation test, and a preservative effectiveness test, as well as drug formulation examples will be illustrated. These examples are presented for the sake of better understanding of the present invention and are not to limit the scope of the present invention.

EXAMPLES

[Storage Stability Test]

It was visually confirmed whether or not appearance of Diquafosol ophthalmic solution had been changed during its storage, and the influence of edetate, which was a chelating agent, on the change of the appearance was examined.

Sample Preparation

Formulation Containing No Chelating Agent 3 g of diquafosol sodium, 0.2 g of sodium hydrogen phosphate, 0.41 g of sodium chloride, 0.15 g of potassium chloride, and 0.0075 g of benzalkonium chloride were dissolved in water so that the resultant solution was 100 mL, to which a pH adjuster was added to adjust the pH to 7.5 and the osmotic pressure ratio to 1.0.

Formulation Containing 0.001 or 0.1% (w/v) Edetate 3 g of diquafosol sodium, 0.2 g of sodium hydrogen phosphate, 0.41 g of sodium chloride, 0.15 g of potassium chloride, 0.001 g or 0.1 g of sodium edetate hydrate, and 0.002 g of benzalkonium chloride were dissolved in water so that the resultant solution was 100 mL, to which a pH adjuster was added to adjust the pH to 7.5 and the osmotic pressure ratio to 1.0.

Test Method

The above-described formulation containing no chelating agent and formulation containing 0.001 or 0.1% (w/v) edetate were each stored in a glass container at 25° C. for three months, and thereafter it was visually confirmed whether or not their appearance had been changed.

Test Results

The test results are indicated in Table 1.

TABLE 1

| formulation | change of appearance |
| --- | --- |
| formulation containing no chelating agent | formation of insoluble precipitates (white particulates) |
| formulation containing 0.001% (w/v) edetate | no change |
| formulation containing 0.1% (w/v) edetate | no change |

As is clear from Table 1, it was confirmed that visible insoluble precipitates were formed in the formulation containing no chelating agent during storage. In contrast, the formulations containing edetate demonstrated that formation of these insoluble precipitates was inhibited.

Discussion

It was suggested that, in Diquafosol ophthalmic solution comprising a chelating agent, insoluble precipitates were not formed in the course of distribution and the course of storage by a patient, or the frequency of formation and the amount of insoluble precipitates in these courses were reduced.

[Filtration Performance Test]

It was confirmed how the filtration performance had changed over time during filtration sterilization of Diquafosol ophthalmic solution, and the influence of edetate, which was a chelating agent, on this change was examined.

Sample Preparation

Formulation Containing No Chelating Agent 30 g of diquafosol sodium, 2 g of sodium hydrogen phosphate, 4.1 g of sodium chloride, 1.5 g of potassium chloride, and 0.075 g of benzalkonium chloride were dissolved in water so that the resultant solution was 1000 mL, to which a pH adjuster was added to adjust the pH to 7.5 and the osmotic pressure ratio to 1.0.

Formulation Containing 0.001% (w/v) Edetate 30 g of diquafosol sodium, 2 g of sodium hydrogen phosphate, 4.1 g of sodium chloride, 1.5 g of potassium chloride, 0.01 g of sodium edetate hydrate, and 0.075 g of benzalkonium chloride were dissolved in water so that the resultant solution was 1000 mL, to which a pH adjuster was added to adjust the pH to 7.5 and the osmotic pressure ratio to 1.0.

Test Method

Each preparation was filtered using, as filtration filters, two-stage hydrophilic PVDF membrane filters (manufactured by Nihon Pall Ltd., Fluorodyne II disc filter φ47 mm, pore size 0.2 μm (model FTKDFL)) at a filtration pressure of 200 kPa and room temperature. The time for filtration and the amount of filtration at this time were measured, and the relation therebetween was plotted.

Test Results

FIG. 1 is a graph showing the results of the filtration performance test conducted for each Diquafosol ophthalmic solution of the formulation containing edetate and the formulation containing no chelating agent, where the vertical axis represents the amount of filtration (g) and the horizontal axis represents the time for filtration (minutes). As is clear from FIG. 1, regarding the formulation containing no chelating agent, reduction of the amount of filtration (reduction of the rate of filtration) was found during filtration sterilization. In contrast, regarding the formulation containing edetate, it was demonstrated that reduction of the rate of filtration was completely inhibited.

Discussion

It was suggested that, as to Diquafosol ophthalmic solution comprising a chelating agent, reduction of the rate of filtration in the course of production (course of filtration sterilization) was completely inhibited, and thus the solution could be subjected to filtration sterilization more efficiently, in comparison to Diquafosol ophthalmic solution comprising no chelating agent. The cause of the reduction of the rate of filtration that has been found regarding Diquafosol ophthalmic solution comprising no chelating agent is considered as clogging with insoluble precipitates (including invisible ones).

[Filtration Performance Test—2]

A comparison and an examination were made on respective influences of a chelating agent which was edetate and a chelating agent other than edetate, on how the filtration performance had changed over time during filtration sterilization of Diquafosol ophthalmic solution.

Sample Preparation

Formulation Containing No Chelating Agent 30 g of diquafosol sodium, 2 g of sodium hydrogen phosphate, 4.1 g of sodium chloride, 1.5 g of potassium chloride, and 0.075 g of benzalkonium chloride were dissolved in water so that the resultant solution was 1000 mL, to which a pH adjuster was added to adjust the pH to 7.5 and the osmotic pressure ratio to 1.0.

Formulation Containing 0.01% (w/v) Edetate 30 g of diquafosol sodium, 2 g of sodium hydrogen phosphate, 4.1 g of sodium chloride, 1.5 g of potassium chloride, 0.1 g of sodium edetate hydrate, and 0.075 g of benzalkonium chloride were dissolved in water so that the resultant solution was 1000 mL, to which a pH adjuster was added to adjust the pH to 7.5 and the osmotic pressure ratio to 1.0.

Formulation Containing 0.01% (w/v) Citric Acid 30 g of diquafosol sodium, 2 g of sodium hydrogen phosphate, 4.1 g of sodium chloride, 1.5 g of potassium chloride, 0.1 g of citric acid monohydrate, and 0.075 g of benzalkonium chloride were dissolved in water so that the resultant solution was 1000 mL, to which a pH adjuster was added to adjust the pH to 7.5 and the osmotic pressure ratio to 1.0.

Formulation Containing 0.01% (w/v) Metaphosphate 30 g of diquafosol sodium, 2 g of sodium hydrogen phosphate, 4.1 g of sodium chloride, 1.5 g of potassium chloride, 0.1 g of sodium metaphosphate, and 0.075 g of benzalkonium chloride were dissolved in water so that the resultant solution was 1000 mL, to which a pH adjuster was added to adjust the pH to 7.5 and the osmotic pressure ratio to 1.0.

Formulation Containing 0.01% (w/v) Polyphosphate 30 g of diquafosol sodium, 2 g of sodium hydrogen phosphate, 4.1 g of sodium chloride, 1.5 g of potassium chloride, 0.1 g of sodium polyphosphate, and 0.075 g of benzalkonium chloride were dissolved in water so that the resultant solution was 1000 mL, to which a pH adjuster was added to adjust the pH to 7.5 and the osmotic pressure ratio to 1.0.

Test Method

Each preparation was filtered using, as filtration filters, two-stage hydrophilic PVDF membrane filters (manufactured by Nihon Pall Ltd., Fluorodyne II disc filter φ25 mm, pore size 0.2 μm (model FTKDFL)) at a filtration pressure of 200 kPa and room temperature. The time for filtration and the amount of filtration per effective filtration area at this time were measured, and the relation therebetween was plotted.

Test Results

Figure 2:
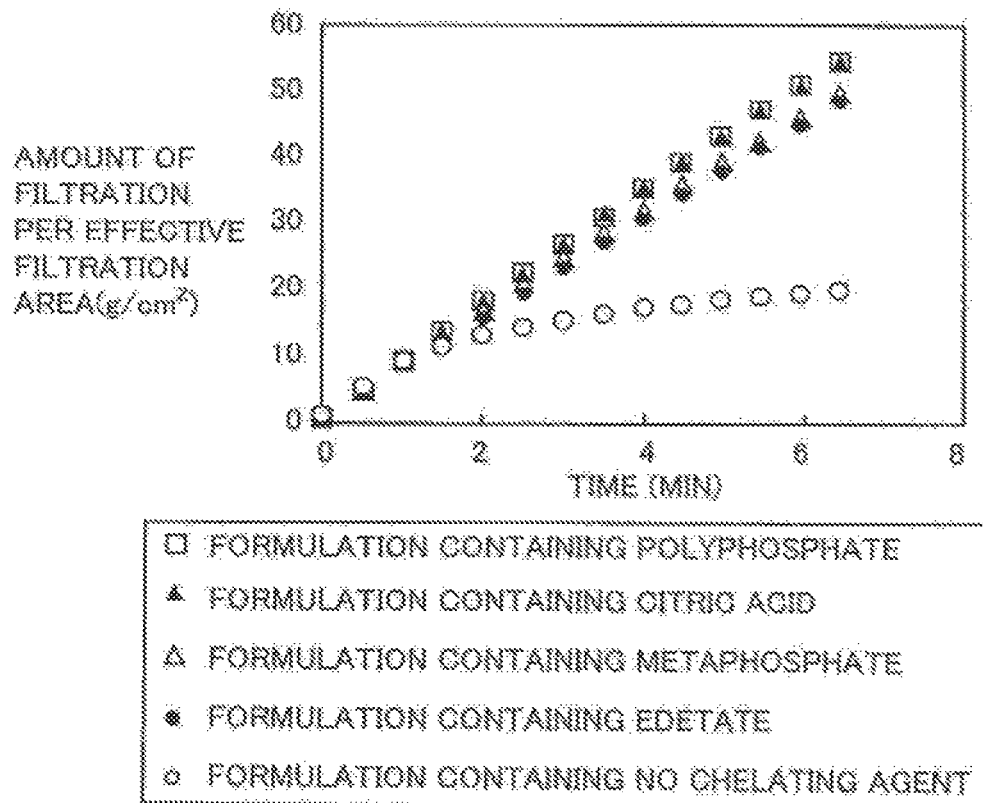
FIG. 2 is a graph showing the results of a filtration performance test conducted for each Diquafosol ophthalmic solution of a formulation containing no chelating agent, or a formulation containing edetate, citric acid, metaphosphate, or polyphosphate, where the vertical axis represents the amount of filtration per effective filtration area (g/cm$^2$) and the horizontal axis represents the time (minutes).

FIG. 2 is a graph showing the results of the filtration performance test conducted for each Diquafosol ophthalmic solution of the formulation containing no chelating agent, or the formulation containing edetate, citric acid, metaphosphate, or polyphosphate, where the vertical axis represents the amount of filtration per effective filtration area (g/cm$^2$) and the horizontal axis represents the time for filtration (minutes). As is clear from FIG. 2, regarding the formulation containing no chelating agent, reduction of the amount of filtration (reduction of the rate of filtration) was found during filtration sterilization. In contrast, as to the formulation containing citric acid, metaphosphate, or polyphosphate, it was demonstrated that reduction of the rate of filtration was completely inhibited, like the formulation containing edetate.

Discussion

It was suggested that, regarding Diquafosol ophthalmic solution comprising a chelating agent, reduction of the rate of filtration in the course of production (course of filtration sterilization) was completely inhibited, and thus the solution could be subjected to filtration sterilization more efficiently relative to Diquafosol ophthalmic solution comprising no chelating agent.

[Eye Irritation Evaluation Test]

The package insert of "DIQUAS (registered trademark) ophthalmic solution 3%" that is Diquafosol ophthalmic solution comprising no chelating agent describes that eye irritation was observed as a side effect in 6.7% of dry-eye patients who have used this ophthalmic solution. Thus, using an n-heptanol-induced corneal epithelial abrasion model showing corneal epithelium disorder like those found in dry-eye patients, it was examined how addition of a chelating agent exerted an influence upon eye irritation by Diquafosol ophthalmic solution.

Sample Preparation

Formulation Containing 3% (w/v) Diquafosol Sodium/Containing No Chelating Agent 3 g of diquafosol sodium, 0.2 g of sodium hydrogen phosphate, 0.41 g of sodium chloride, 0.15 g of potassium chloride, and 0.0075 g of benzalkonium chloride were dissolved in water so that the resultant solution was 100 mL, to which a pH adjuster was added to adjust the pH to 7.2 to 7.8 and the osmotic pressure ratio to 1.0 to 1.1.

Formulation Containing 3% (w/v) Diquafosol Sodium/Containing Edetate 3 g of diquafosol sodium, 0.2 g of sodium hydrogen phosphate, 0.41 g of sodium chloride, 0.15 g of potassium chloride, 0.01 g of sodium edetate hydrate, and 0.002 g of benzalkonium chloride were dissolved in water so that the resultant solution was 100 mL, to which a pH adjuster was added to adjust the pH to 7.2 to 7.8 and the osmotic pressure ratio to 1.0 to 1.1.

Formulation Containing 8% (w/v) Diquafosol Sodium/Containing No Chelating Agent 8 g of diquafosol sodium, 0.2 g of sodium hydrogen phosphate, and 0.0075 g of benzalkonium chloride were dissolved in water so that the resultant solution was 100 mL, to which a pH adjuster was added to adjust the pH to 7.2 to 7.8 and the osmotic pressure ratio to 1.0 to 1.1.

Formulation Containing 8% (w/v) Diquafosol Sodium/Containing Edetate 8 g of diquafosol sodium, 0.2 g of sodium hydrogen phosphate, 0.01 g of sodium edetate hydrate, and 0.002 g of benzalkonium chloride were dissolved in water so that the resultant solution was 100 mL, to which a pH adjuster was added to adjust the pH to 7.2 to 7.8 and the osmotic pressure ratio to 1.0 to 1.1.

Vehicle 0.2 g of sodium hydrogen phosphate, 0.75 g of sodium chloride, 0.15 g of potassium chloride, and 0.0075 g of benzalkonium chloride were dissolved in water so that the resultant solution was 100 mL, to which a pH adjuster was added to adjust the pH to 7.2 to 7.8 and the osmotic pressure ratio to 1.0 to 1.1.

Test Method

After treatment with n-heptanol was given to a cornea of the rabbit's left eye (for 1 minute), the corneal epithelium was peeled. After 16 to 18 hours, a vehicle, a formulation containing 3% (w/v) diquafosol sodium/containing no chelating agent, or a formulation containing 3% (w/v) diquafosol sodium/containing edetate was applied once to the eye (50 μL/eye). Then, the number of eye-blinking times for 1 minute after the application was measured and the symptoms related to pain during the application were observed. The signs related to pains such as closed eyes and half-closed eyes for 5 minutes after the application were subsequently observed (four examples in one group).

About 1 hour after the above-described observation, a vehicle, a formulation containing 8% (w/v) diquafosol sodium/containing no chelating agent or a formulation containing 8% (w/v) diquafosol sodium/containing edetate was applied once (50 μm/eye) to the corresponding rabbit's left eye to which the vehicle, the formulation containing 3% (w/v) diquafosol sodium/containing no chelating agent, or the formulation containing 3% (w/v) diquafosol sodium/containing edetate was applied. Then, a similar observation was carried out.

Test Results

The test results are indicated in Tables 2 and 3.

TABLE 2

| formulation | | vehicle | formulation containing 3% (w/v) diquafosol sodium/ containing no chelating agent | formulation containing 3% (w/v) diquafosol sodium/ containing edetate |
|---|---|---|---|---|
| | number of examples | 4 | 4 | 4 |
| number of eye-blinking times (1 min after application) | number of eye-blinking times (times/min) (mean ± SD) | 1.0 ± 1.2 | 2.5 ± 2.4 | 1.8 ± 1.5 |
| | signs related to pain | — | 2 examples of half-closed eyes (10 sec and 3 sec) | — |

TABLE 2-continued

| formulation | | vehicle | formulation containing 3% (w/v) diquafosol sodium/ containing no chelating agent | formulation containing 3% (w/v) diquafosol sodium/ containing edetate |
|---|---|---|---|---|
| symptoms related to pain (after 1 to 5 min from application) | half-closed eyes/ closed eyes | 1 example (15 sec) | 4 examples (intermittent) | 1 example (10 sec) |

TABLE 3

| formulation | | vehicle | formulation containing 8% (w/v) diquafosol sodium/ containing no chelating agent | formulation containing 8% (w/v) diquafosol sodium/ containing edetate |
|---|---|---|---|---|
| number of eye-blinking times (1 min after application) | number of examples | 4 | 4 | 4 |
| | number of eye-blinking times (times/min) (mean ± SD) | 1.5 ± 1.7 | 2.8 ± 1.7 | 2.0 ± 2.4 |
| | signs related to pain | — | 2 examples of half-closed eyes (10 sec × 5 times and 6 sec) | — |
| symptoms related to pain (after 1 to 5 min from application) | half-closed eyes/ closed eyes | 1 example (5 sec) | 3 examples (intermittent or continuous) | — |

As is clear from Tables 2 and 3, regarding the formulation containing no chelating agent, half-closed eyes were observed in two of four examples in 1 minute after the application also in the case where 3% (w/v) or 8% (w/v) diquafosol sodium was applied. This tendency was further more remarkable after 1 to 5 minutes from the application. In contrast, regarding the formulation containing edetate, half-closed eyes/closed eyes were observed in one of four examples after 1 to 5 minutes from the application only in the case where 3% (w/v) diquafosol sodium was applied, but the occurrence frequency was approximately the same as that of the group to which a vehicle was applied.

Discussion

As described above, regarding Diquafosol ophthalmic solution, it was suggested that half-closed eyes/closed eyes representing signs related to pain were caused with high frequency in an n-heptanol-induced corneal epithelial abrasion model showing corneal epithelium disorder like those found in dry-eye patients, while addition of a chelating agent to this ophthalmic solution allowed a decrease in occurrence frequency of these events to the level achieved in the case where the vehicle was applied. In other words, it is considered that addition of a chelating agent allows reduction of eye irritation as a side effect observed with certain frequency when Diquafosol ophthalmic solution containing no chelating agent is applied to a dry-eye patient.

[Preservative Effectiveness Test]

A preservative effectiveness test was conducted in order to confirm the influence of a chelating agent on the preservative effectiveness of Diquafosol ophthalmic solution.

Sample Preparation

Formulation Containing No Chelating Agent 3 g of diquafosol sodium, 0.2 g of sodium hydrogen phosphate, 0.41 g of sodium chloride, 0.15 g of potassium chloride, and 0.0036 g of benzalkonium chloride were dissolved in water so that the resultant solution was 100 mL, to which a pH adjuster was added to adjust the pH to 7.2 to 7.8 and the osmotic pressure ratio to 1.0 to 1.1.

Formulation Containing 0.01% (w/v) Edetate 3 g of diquafosol sodium, 0.2 g of sodium hydrogen phosphate, 0.41 g of sodium chloride, 0.15 g of potassium chloride, 0.01 g of sodium edetate hydrate, and 0.0024 g of benzalkonium chloride were dissolved in water so that the resultant solution was 100 mL, to which a pH adjuster was added to adjust the pH to 7.2 to 7.8 and the osmotic pressure ratio to 1.0 to 1.1.

Test Method

The preservative effectiveness test was conducted in accordance with the preservative effectiveness test method defined by the Japanese Pharmacopoeia, 15th edition. For this test, the following test microorganisms were used: *Esherichia Coli* (*E. coli*), *Pseudomonas aeruginosa* (*P. aeruginosa*), *Staphylococcus aureus* (*S. aureus*), *Candida albicans* (*C. albicans*), and *Aspergillus braziliensis* (*A. braziliensis*).

Test Results

The test results are indicated in Table 4.

TABLE 4

| Ingredients | | | formulation containing no chelating agent | formulation containing edetate |
|---|---|---|---|---|
| diquafosol sodium | | | 3% | 3% |
| sodium hydrogen phosphate | | | 0.2% | 0.2% |
| sodium chloride | | | 0.41% | 0.41% |
| potassium chloride | | | 0.15% | 0.15% |
| sodium edetate hydrate | | | — | 0.01% |
| benzalkonium chloride | | | 0.0036% | 0.0024% |
| test results (log reduction) | *E. coli* | 2 wks | N.D. | N.D. |
| | | 4 wks | N.D. | N.D. |
| | *P. aeruginosa* | 2 wks | N.D. | N.D. |
| | | 4 wks | 4.2 | N.D. |
| | *S. aureus* | 2 wks | N.D. | N.D. |
| | | 4 wks | N.D. | N.D. |
| | *C. albicans* | 2 wks | 5.6 | >4.3 |
| | | 4 wks | N.D. | N.D. |
| | *A. braziliensis* | 2 wks | 3.0 | 2.9 |
| | | 4 wks | 5.1 | >4.4 |
| Conclusions | | | Not passed* | Passed |

N.D.: not detected
*The formulation containing no chelating agent did not pass the criterion because growth of *P. aeruginosa* was found in the 4th week.

The test results in Table 4 indicate to what extent the number of viable microorganisms has decreased in the test relative to the number of inoculated microorganisms, based on log reduction. For example, the log reduction "1" indicates that the number of viable microorganisms in the test has decreased to 10% relative to the number of inoculated microorganisms.

As indicated in Table 4, the formulation containing no chelating agent did not pass the criterion (Category IA) of the preservative effectiveness test of the Japanese Pharmacopoeia even though the concentration of blended benzalkonium chloride serving as a preservative was 0.0036% (w/v). In contrast, the formulation containing edetate passed the above-referenced criterion even though the concentration of blended benzalkonium chloride was 0.0024% (w/v). Accordingly, the formulation containing edetate exhibited remarkably enhanced preservative effectiveness, in comparison to the formulation containing no chelating agent.

Discussion

The above-described results suggest that addition of a chelating agent to Diquafosol ophthalmic solution significantly enhances the preservative effectiveness of the solution. In other words, it is considered that the present ophthalmic solution allows reduction of the concentration of the preservative in the ophthalmic solution in comparison to Diquafosol ophthalmic solution containing no chelating agent.

PREPARATION EXAMPLES

Preparation examples will now be given to describe the drug of the present invention more specifically. The present invention, however, is not limited solely to these preparation examples.

Formulation Example 1: Ophthalmic Solution (3% (w/v))

In 100 ml

| | |
|---|---|
| diquafosol sodium | 3 g |
| sodium hydrogen phosphate | 0.1 to 0.5 g |
| sodium chloride | 0.01 to 1 g |
| potassium chloride | 0.01 to 1 g |
| sodium edetate hydrate | 0.0001 to 0.1 g |
| sterile purified water | q.s. |

Diquafosol sodium and other ingredients listed above are added to sterile purified water and they are mixed sufficiently so that this ophthalmic solution can be prepared.

Formulation Example 2: Ophthalmic Solution (3% (w/v))

In 100 ml

| | |
|---|---|
| diquafosol sodium | 3 g |
| sodium hydrogen hydrate | 0.1 to 0.5 g |
| sodium chloride | 0.01 to 1 g |
| potassium chloride | 0.01 to 1 g |
| BAK-$C_{12}$ | 0.1 to 10 g |
| sodium edetate hydrate | 0.0001 to 0.1 g |
| sterile purified water | q.s. |

Diquafosol sodium and other ingredients listed above are added to sterile purified water and they are mixed sufficiently so that this ophthalmic solution can be prepared.

Formulation Example 3: Ophthalmic Solution (3% (w/v))

In 100 ml

| | |
|---|---|
| diquafosol sodium | 3 g |
| sodium hydrogen phosphate | 0.1 to 0.5 g |
| sodium chloride | 0.01 to 1 g |
| potassium chloride | 0.01 to 1 g |
| BAK-$C_{12}$ | 0.1 to 10 g |
| citric acid monohydrate | 0.0001 to 0.1 g |
| sterile purified water | q.s. |

Diquafosol sodium and other ingredients listed above are added to sterile purified water and they are mixed sufficiently so that this ophthalmic solution can be prepared.

Formulation Example 4: Ophthalmic Solution (3% (w/v))

In 100 ml

| | |
|---|---|
| diquafosol sodium | 3 g |
| sodium hydrogen phosphate | 0.1 to 0.5 g |
| sodium chloride | 0.01 to 1 g |
| potassium chloride | 0.01 to 1 g |
| BAK-$C_{12}$ | 0.1 to 10 g |
| sodium metaphosphate | 0.0001 to 0.1 g |
| sterile purified water | q.s. |

Diquafosol sodium and other ingredients listed above are added to sterile purified water and they are mixed sufficiently so that this ophthalmic solution can be prepared.

Formulation Example 5: Ophthalmic Solution (3% (w/v))

In 100 ml

| | |
|---|---|
| diquafosol sodium | 3 g |
| sodium hydrogen phosphate | 0.1 to 0.5 g |
| sodium chloride | 0.01 to 1 g |
| potassium chloride | 0.01 to 1 g |
| BAK-$C_{12}$ | 0.1 to 10 g |
| sodium polyphosphate | 0.0001 to 0.1 g |
| sterile purified water | q.s. |

Diquafosol sodium and other ingredients listed above are added to sterile purified water and they are mixed sufficiently so that this ophthalmic solution can be prepared.

INDUSTRIAL APPLICABILITY

Regarding Diquafosol ophthalmic solution comprising a chelating agent at a concentration of 0.0001 to 1% (w/v), formation of insoluble precipitates found in Diquafosol ophthalmic solution during storage of the solution, as well as deterioration of the filtration performance in the course of production (course of filtration sterilization), have been inhibited. Further, in Diquafosol ophthalmic solution comprising a chelating agent, reduction of eye irritation and enhancement of the preservative effectiveness have been confirmed, in comparison to Diquafosol ophthalmic solution comprising no chelating agent. Accordingly, the present invention has physicochemical properties that are stable during the courses of production and distribution as well as the course of storage by a patient, allows reduction of eye irritation, and also has excellent preservative effectiveness. In particular, since degradation of the filtration performance in the course of production (course of filtration sterilization) is inhibited, Diquafosol ophthalmic solution comprising a chelating agent can be subjected to efficient filtration sterilization in the course of production, thereby contributing to a decrease in production cost.

The invention claimed is:

1. A method for treating dry eye comprising applying to corneal epithelium disorder found in a dry-eye patient an aqueous ophthalmic solution consisting of diquafosol or a salt thereof at a concentration of 0.1 to 10% (w/v) and a chelating agent at a concentration of 0.0001 to 1% (w/v) and optionally at least one other agent of a buffer agent, isotonizing agent, surfactant or pH adjuster, wherein the surfactant is selected from the group consisting of polyoxyl 40 stearate and polyoxyethylene hydrogenated castor oil, and wherein the chelating agent is at least one type selected from the group consisting of edetic acid, citric acid, metaphosphoric acid, pyrophosphoric acid, polyphosphoric acid, malic acid, tartaric acid, phytic acid, and salts thereof.

2. The method according to claim 1, wherein the chelating agent is at least one type selected from the group consisting of edetic acid, citric acid, metaphosphoric acid, polyphosphoric acid, and salts thereof.

3. The method according to claim 1, wherein the chelating agent is a salt of edetic acid.

4. The method according to claim 1, wherein the chelating agent is at a concentration of 0.0005 to 0.5% (w/v) in the ophthalmic solution.

5. The method according to claim 1, wherein the chelating agent is at a concentration of 0.001 to 0.1% (w/v) in the ophthalmic solution.

6. The method according to claim 1, wherein diquafosol or a salt thereof is at a concentration of 1 to 10% (w/v) in the ophthalmic solution.

7. The method according to claim 1, wherein diquafosol or a salt thereof is at a concentration of 3% (w/v) in the ophthalmic solution.

8. The method according to claim 1, wherein the chelating agent is a salt of edetic acid, the chelating agent is at a concentration of 0.001 to 0.1% (w/v) in the ophthalmic solution, and diquafosol or a salt thereof is at a concentration of 3% (w/v) in the ophthalmic solution.

9. The method according to claim 1, wherein the buffer agent is at least one type selected from the group consisting of sodium phosphate, sodium hydrogen phosphate, sodium dihydrogen phosphate, sodium acetate, and epsilon aminocaproic acid.

10. The method according to claim 1, wherein the isotonizing agent is at least one type selected from the group consisting of sodium chloride, potassium chloride, and concentrated glycerin.

* * * * *